United States Patent [19]

Cartmill

[11] Patent Number: 5,526,536
[45] Date of Patent: Jun. 18, 1996

[54] ENDO-SURGERY GLOVE AND SEAL

[75] Inventor: John A. Cartmill, Cleveland, Ohio

[73] Assignee: Ethicon, Inc., Somerville, N.J.

[21] Appl. No.: 295,181

[22] Filed: Aug. 24, 1994

Related U.S. Application Data

[63] Continuation of Ser. No. 117,520, Sep. 3, 1993, abandoned.

[51] Int. Cl.⁶ .......................... A41D 13/10; A41D 19/00
[52] U.S. Cl. .................................. 2/161.7; 2/162; 2/168
[58] Field of Search ....................... 2/DIG. 3, 162,
  2/168, 159, 158, 161.1, 161.6, 161.7, 160,
  16, 270, 901, 170; 128/DIG. 20; 602/13;
  604/96, 99, 167, 256

[56] References Cited

U.S. PATENT DOCUMENTS

| | | | |
|---|---|---|---|
| 732,360 | 6/1903 | Lindsay | 2/168 |
| 1,602,027 | 10/1926 | Kennedy | 2/19 |
| 2,582,648 | 1/1952 | Mowbray | 2/DIG. 3 X |
| 3,332,415 | 7/1967 | Ericson | 128/DIG. 20 |
| 4,121,312 | 10/1978 | Penney | 9/308 |
| 4,173,218 | 11/1979 | Cronin | 128/DIG. 20 |
| 4,281,647 | 8/1981 | Antypas | 128/DIG. 20 |
| 4,302,852 | 12/1981 | Joung. | |
| 4,522,197 | 6/1985 | Hasegawa | 128/DIG. 20 |
| 4,619,250 | 10/1986 | Hasegawa | 128/DIG. 20 |
| 4,706,658 | 11/1987 | Cronin | 128/DIG. 20 |
| 4,807,606 | 2/1989 | Hasegawa et al. | 128/DIG. 20 |
| 5,100,420 | 3/1992 | Green et al. | 606/143 |
| 5,104,383 | 4/1992 | Shichman | 604/167 |
| 5,171,249 | 12/1992 | Stefanchik et al. | 606/142 |
| 5,197,955 | 3/1993 | Stephens et al. | 604/167 |
| 5,297,541 | 3/1994 | Hensey | 601/40 |

FOREIGN PATENT DOCUMENTS

| | | | |
|---|---|---|---|
| 1260201 | 9/1989 | Canada | 2/168 |
| 2145323 | 3/1985 | United Kingdom | 2/16 |
| 2017079 | 10/1992 | WIPO | 2/159 |

*Primary Examiner*—Amy B. Vanatta
*Attorney, Agent, or Firm*—Matthew S. Goodwin

[57] ABSTRACT

A surgical glove for endoscopic surgical procedures is disclosed. In the preferred embodiment, the surgical glove has an inflatable wrist section, which when inflated, provides a seal between the surgeon's gloved hand and the body wall for obstructing the passage of gas from the abdominal cavity during endoscopic surgery. The inflated glove wrist section will conform to the surgeon's hand and the abdominal cavity wall to provide the seal and yet allow the surgeon's hand to move in an inward or outward direction transversely to the abdominal wall.

2 Claims, 3 Drawing Sheets

ENDO-SURGERY GLOVE AND SEAL

This is a continuation, of application Ser. No. 08/117,520, filed Sep. 3, 1993, now abandoned.

FIELD OF THE INVENTION

The present field of invention relates to the field of surgical devices. More particularly, it relates to such a device for providing a seal during endoscopic surgery. Specifically, it relates to an endoscopic glove which can provide such a seal.

BACKGROUND OF THE INVENTION

In the practice of abdominal surgery, which requires the examination and manipulation of intraperitoneal and extra-peritoneal organs and tissues, surgeons most often employ a long established technique of opening the abdominal wall with an incision large enough to accommodate instruments required, as well as the surgeon's hand, and to allow removal of the diseased organ or portions thereof. The advantages of this technique include a large degree of freedom of motion for successfully completing the procedure, sufficient space for mechanical leverage which may be necessary, and above all, tactile feedback response to the surgeon when using his hands to feel the texture, temperature, and physical response of the tissue under treatment. The disadvantages of this traditional technique, however, include long healing and recuperative time with considerable post-operative pain, and adhesion formation which can cause pain and bowel obstruction. Additionally, the traditional technique may increase the complexity of later surgery and postoperative morbidity, and the probability of unsightly large scars remaining after the procedure is completed.

In order to overcome the disadvantages of the traditional abdominal surgery method using a large incision, laparoscopic techniques have been developed which use several smaller puncture openings in the abdominal wall. These openings are used to inflate the abdominal cavity with a gas to elevate the abdominal wall away from the organs and allow room for the manipulation of the organs. The openings also provide means to introduce light generating and optical viewing instruments to observe the abdominal cavity and to manipulate the organs in order to accomplish the desired results. This laparoscopic technique is becoming widely accepted because of its many advantages. These advantages include reduced adhesions, shorter recovery time, and less post-operative pain. There are also some disadvantages. For example, there are limitations on freedom to manipulate organs, and the surgeon's viewing ability, although magnified with the aid of a laparoscope, lacks depth perception. Most importantly, there is a lack of tactile feedback of the tissue through the surgeons hands. Also, when a tissue specimen must be removed, a larger opening must be made in the abdominal wall near the end of the procedure, causing loss of gas pressure, collapse of the abdominal wall, and loss of interior working and viewing space.

The laparoscopic technique uses smaller puncture openings in the abdominal wall as described. These openings are usually made with a puncture device called a trocar. The trocar point and attached shaft are usually contained in a hollow circular tube which remains in the abdominal wall after puncture and through which other instrument shafts are passed to be used in the operating procedure. A sealing feature must be included in the trocar cannula body in order to maintain the gas pressure as described above. Various sizes and shapes of instruments are used in these procedures and sealing between the instruments and the trocar body must be achieved. Also, internal sealing is required within the instrument body to avoid gas leakage. The importance of these sealing requirements is indicated by their inclusion in endoscopic instrument patents. For example, U.S. Pat. Nos. 5,104,383 and 5,197,955, describe sealing mechanisms between trocars and instruments passed through them. Also, the endoscopic instruments themselves contain internal sealing means to reduce the loss of gas pressure in the abdominal cavity. U.S. Pat. Nos. 5,100,420 and 5,171,249, describe internal sealing means in endoscopic instruments.

Combining the advantages of the traditional and the laparoscopic techniques for abdominal surgery is the laparoscopic assisted procedure. In this procedure, the normal laparoscopic small puncture openings are made with the exception that one opening is made late in the procedure and large enough to allow a surgeon's hand to pass through the abdominal wall in order to remove tissue or deliver a mobile organ for surgery. When this larger opening is made, gas pressure is lost and the procedure must be completed by using a plug usually made of gauze to seal the opening to allow reinflation. This sequence of removing the plug, losing gas pressure, performing a surgical step, replugging the opening, and reinflating the abdominal cavity can be repeated several times before the surgical procedure is completed.

Surgical gloves that fit a surgeon's hand are well known in the art. For Example, see U.S. Pat. No. 732,360, which describes an early method for manufacturing surgical gloves. U.S. Pat. No. 4,302,852 describes surgical glove materials and method of manufacture. Surgical gloves in use today are sufficient for use in traditional surgical procedures; however, for use in laparoscopic assisted procedures, unique structural requirements are desirable.

Accordingly, it is an object of the present invention to utilize the laparoscopic method for surgery, which allows for quicker recovery than the traditional method, yet allows the surgeon to obtain tactile feedback during surgery to determine directly the information needed to successfully conclude the procedure as well as to allow removal of desired bodily tissue. It would be desirable if this object could be achieved when the surgeon uses his hand for tactile feedback, and that when the surgeon introduces his hand into the body cavity, gas pressure is maintained inside the body cavity. Furthermore, it would be particularly desirable if the gas pressure could be maintained when the surgeon is wearing a surgical glove specifically designed to provide a seal between the surgeon's gloved hand and the opening in the body wall. Lastly, it would be desirable if such a specifically designed glove conforms to the wrist and distal forearm of the surgeon, so that the surgeon's manual dexterity is not compromised.

SUMMARY OF THE INVENTION

The foregoing objects of the invention are now achieved with the use of a new surgical glove. The surgeon's gloved hand is capable of maintaining gas pressure during a laparoscopic assisted procedure. The glove has an inflatable wrist section, and inflation means attached to the inflatable wrist section for selectively inflating or deflating the inflatable wrist section of the glove. The inflatable wrist section is preferably located at the glove wrist area of the surgeon's arm, which is the smallest diameter of the arm section between the forearm and the hand. When the inflatable wrist section of the glove is inflated, it provides a uniform diameter from the surgeon's hand to the forearm. This feature provides sealing between the surgeon's hand and the walls of the abdominal cavity while allowing motion of the surgeon's hand into and out of the cavity.

Another advantage of the present invention is that the inflatable surgeon's glove can be made using commercially available biocompatible polymeric materials.

In yet another advantage of the present invention, the device can be made utilizing current manufacturing technology for inflatable structures.

The inflatable surgeon's glove of this invention can be used during any surgical procedure requiring the insufflation of the abdominal cavity during surgery, particularly laparoscopic assisted surgical procedures.

BRIEF DESCRIPTION OF THE DRAWINGS

An embodiment of the invention is described by way of example with reference to the accompanying drawings in which.

DETAILED DESCRIPTION OF THE PREFERRED EMBODIMENTS

Figure 1:
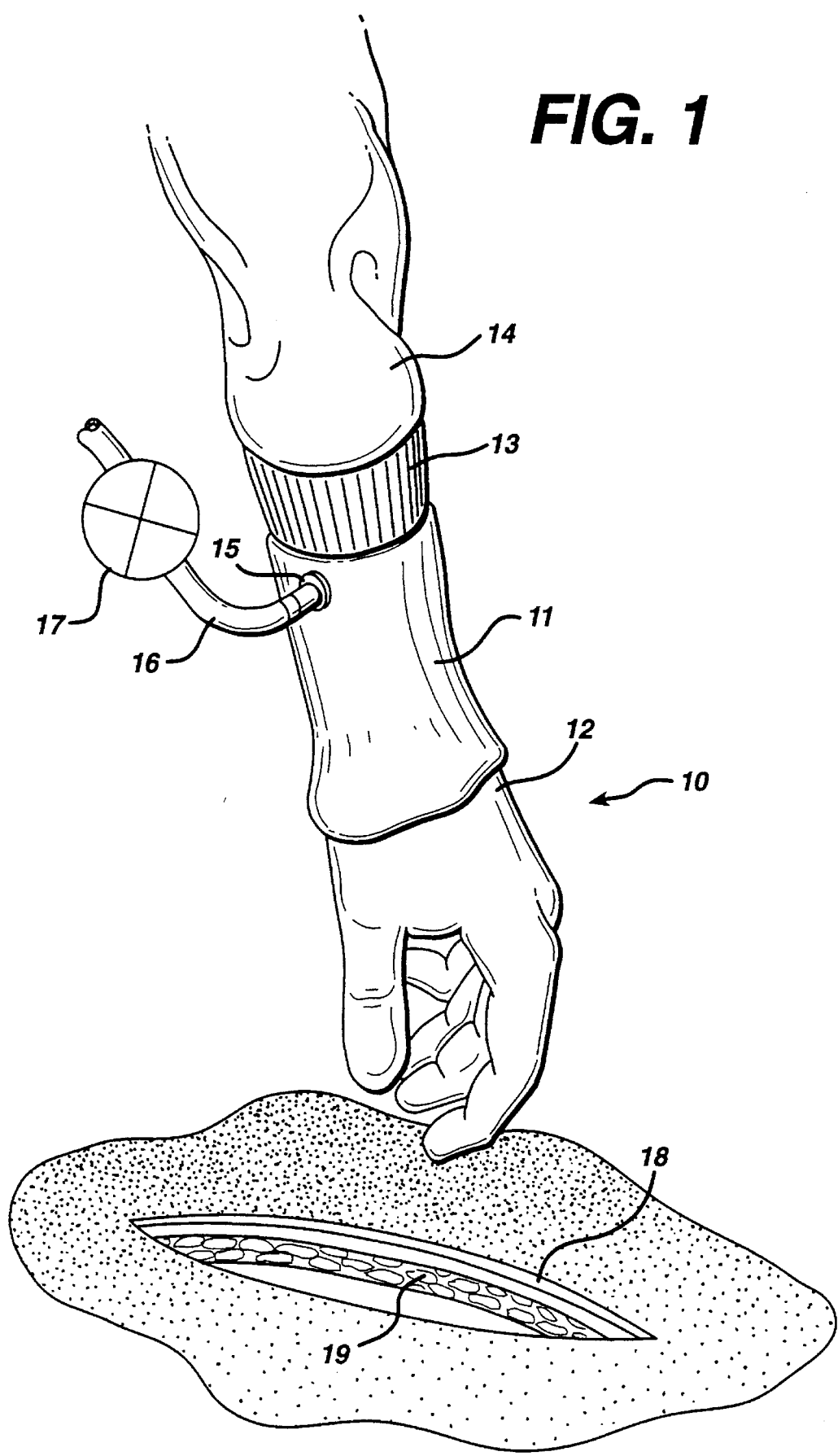
FIG. 1 is a diagrammatic view of a preferred surgeon's glove of this invention where the inflatable wrist section is in its deflated state, and the surgeon's hand is inserted into the glove and positioned prior to entry into an abdominal wall incision.
Figure 2:
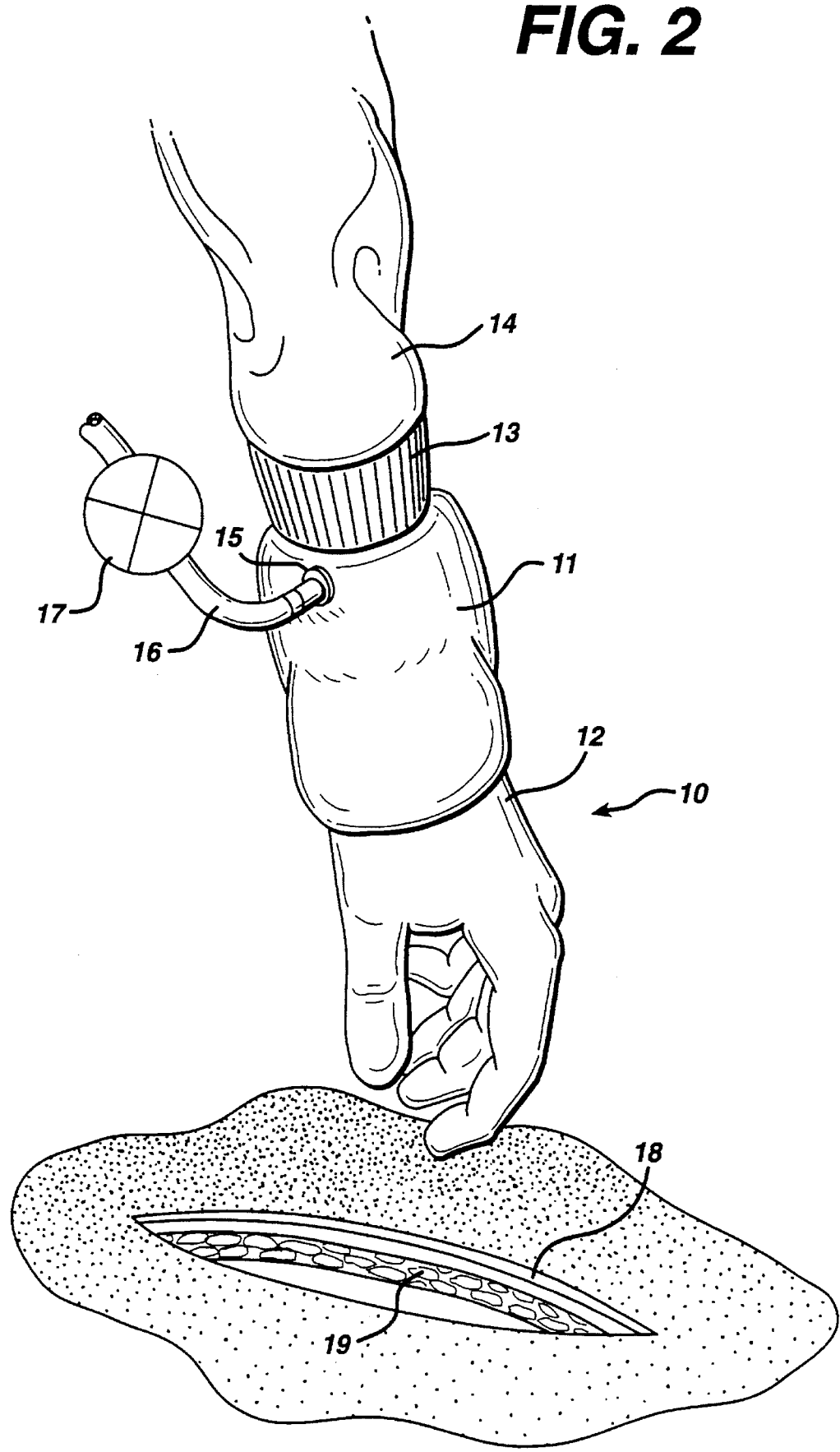
FIG. 2 is the same device with the inflatable wrist section of the glove in its inflated state.
Figure 3:
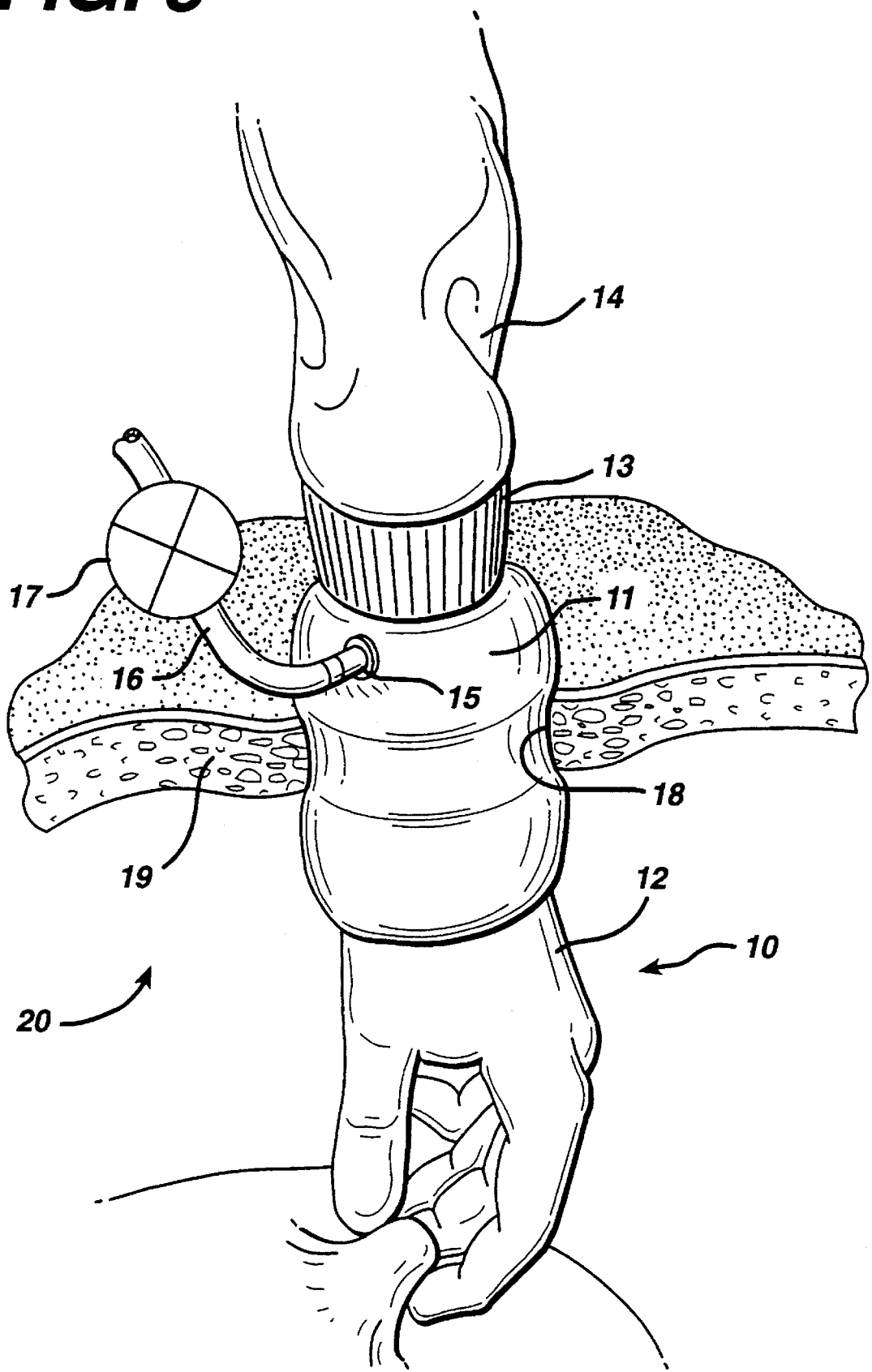
FIG. 3 is a diagrammatic view of the device shown in FIG. 2 inserted through the incision and functioning as a gas seal between the abdominal wall and the surgeon's wrist and arm.

In one of the preferred embodiments as shown at FIGS. 1 through 3, the endo-surgery glove 10 has an inflatable balloon section 11 which can terminate at the proximal end of the glove and is of sufficient length to surround the surgeon's wrist from the widest part of the hand 12 to the distal forearm 13. The endo-surgery glove of the preferred embodiment is of sufficient length as to cover the surgeon's sterile gown sleeve 14, the same length as a surgeon's normal glove. The inflatable balloon section is made of the same material as the glove. An inflation means 15 for inflating and deflating the inflatable section 11 is attached to the inflatable section 11. The inflatable means 15 includes a tubular conduit 16, which contains a valve 17 shown schematically to selectively inflate the inflatable section from a source of pressurized gas, e.g. $CO_2$ (the source for pressurized gas is not shown), or deflate the endo-surgery glove inflatable section 11 when desired. Such valves 17 are commonly used in the medical device field and are known to someone skilled in the art.

The function of the endo-surgical glove 10 is illustrated in FIGS. 1 through 3. When the inflatable section 11 of the endo-surgical glove 10 is deflated as shown on FIG. 1 or when the inflatable section 11 is inflated as shown in FIG. 2, the surgeon can insert his hand through the incision 18 in the abdominal wall 19. FIG. 1 shows the inflatable; section of the endo-surgical glove in its deflated state and FIG. 2 shows the section in its inflated state. The sealing function is shown on FIG. 3 where the inflatable section 11 presses against the abdominal wall 19 along the edges of its incision 18. The pressing action is provided by the internal pressure of the pressurizing media in the inflatable section 11 causing the inflatable section 11 to balloon outward from the surgeon's wrist and touch the abdominal wall 19. The surgeon can move his hand in an inward or outward direction transversely to the abdominal wall while escape of gas from the abdominal cavity is prevented by the seal provided by the inflatable section 11 of the endo-surgical glove 10.

The inflatable section 11 of the endo-surgical glove 10 is preferably made from a separate piece of polymeric glove material and bonded to the glove using techniques known to persons skilled in the art. The inflatable balloon section can be attached to the surgeon's glove using an elastomeric adhesive having high flexibility and compatibility with the glove material. An example of such an adhesive is BOSTICK 2003 adhesive sold commercially by Bostick, Inc.

The overall dimensions of the inflatable sealing section 11 of the surgical glove, when inflated, include a minimum outside circumference of about 10 to 12 inches and an approximate overall length of about 5 to 6 inches. The thickness of the inflatable section 11 can be approximately the same as the surgeon's glove thickness of approximately 0.004 to 0.008 inches. The glove thickness is related to the material used.

The endo-surgical glove 10 is preferably composed of a biocompatable polymer, including but not limited to latex rubber, polyethylene polymers, or polypropylene polymers. The material should be capable of being inflated and deflated numerous times without losing its originally formed shape and return to its original deflated shape as shown in FIG. 1.

The inflation pressure for the inflated section 11 of the endo-surgical glove 10 should be at a minimum value greater than the normal range of gas pressure used in the abdominal cavity 20 which usually ranges from 8 to 15 mm mercury (0.14 to 0.28 psi).

Although this invention has been specifically described with respect to the preferred embodiments, numerous additional embodiments feasible to those skilled in the art are well within the spirit and scope of the invention as defined by the claims set forth below.

What is claimed is:

1. A surgical glove composed of a biocompatible polymer to cover a surgeon's hand from the surgeon's distal forearm, said glove having a glove thickness of about 0.004 to 0.008 inches and having an inflatable wrist section thereon extending from said distal forearm to the widest part of said surgeon's hand, and a plurality of fingers with fingertips extending from said inflatable wrist section, wherein said fingers are not interconnected with each other at or adjacent said fingertips, said fingers being non-inflatable and sized to substantially conform to the corresponding fingers of said surgeon's hand; and inflation means attached to said inflatable wrist section for selectively inflating or deflating said inflatable wrist section of said glove.

2. A surgical glove as described in claim 1 wherein said polymer is a latex rubber, polyethylene or polypropylene.

* * * * *